(12) United States Patent
Pansiera

(10) Patent No.: US 7,662,118 B2
(45) Date of Patent: Feb. 16, 2010

(54) ORTHOTIC HINGE SYSTEM WITH SPRING-BIASED PAWL CONTROL OF RATCHET MEMBER

(75) Inventor: Timothy Pansiera, Weaverville, NC (US)

(73) Assignee: Fillauer, LLC, Chattanooga, TN (US)

( * ) Notice: Subject to any disclaimer, the term of this patent is extended or adjusted under 35 U.S.C. 154(b) by 183 days.

(21) Appl. No.: 11/804,645

(22) Filed: May 18, 2007

(65) Prior Publication Data

US 2008/0287847 A1 Nov. 20, 2008

(51) Int. Cl.
*A61F 5/00* (2006.01)
(52) U.S. Cl. .......................................... 602/16; 602/23
(58) Field of Classification Search .................. 602/5, 602/16, 20–23, 26–27; 128/882
See application file for complete search history.

(56) References Cited

U.S. PATENT DOCUMENTS

| | | | |
|---|---|---|---|
| 2,943,622 A * | 7/1960 | Nelson | 602/16 |
| 4,502,472 A | 3/1985 | Pansiera | |
| 4,928,676 A | 5/1990 | Pansiera | |
| 5,776,086 A * | 7/1998 | Pansiera | 602/16 |
| 6,960,175 B1 * | 11/2005 | Myers | 602/16 |

* cited by examiner

*Primary Examiner*—Michael A. Brown
(74) *Attorney, Agent, or Firm*—Chambliss, Bahner & Stophel, P.C..

(57) ABSTRACT

The invention relates to an orthopedic hinge system, including an outer and an inner lateral base, each substantially complemental in peripheral dimension to each other, the bases each having a major vertical axis, the inner base having a recess. Also included is an elongate distal member having a semi-circular pivot end including, upon a portion of the end, ratchet teeth pointing in a counter-clockwise direction, the pivot end rotationally secured to both of the bases. Further included is an elongate proximal member having a transverse end element proportioned for complemental securement within the recess of the inner base, transverse end element including an axis of rotation co-linear with an axis of rotation of the distal member and defining an axis of rotation of the pivot end of the distal member. The system also includes a cam lever including a pawl surface having teeth pointing in a clockwise direction and, upon contact with the ratchet teeth of the distal member, then complemental therewith, the lever having an axis of rotation co-linear with a second axis within a transverse end element of the proximal member, the lever also including a radial projection disposed radially oppositely from the pawl surface to which an end of a biasing spring is attached.

5 Claims, 10 Drawing Sheets

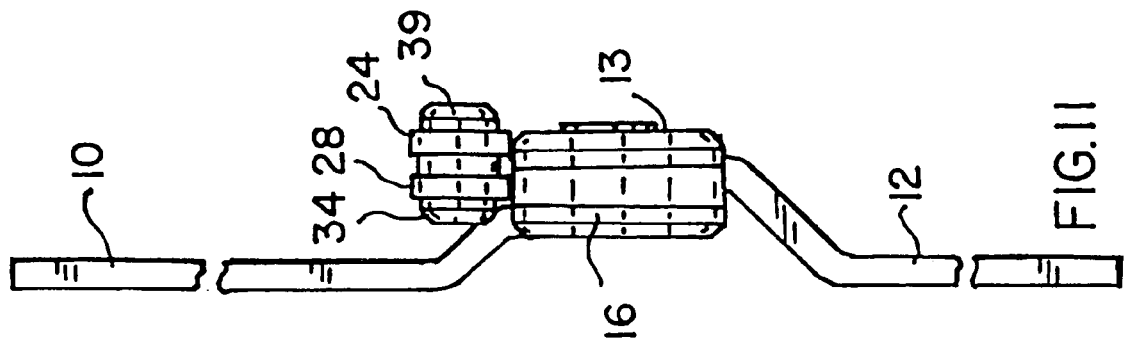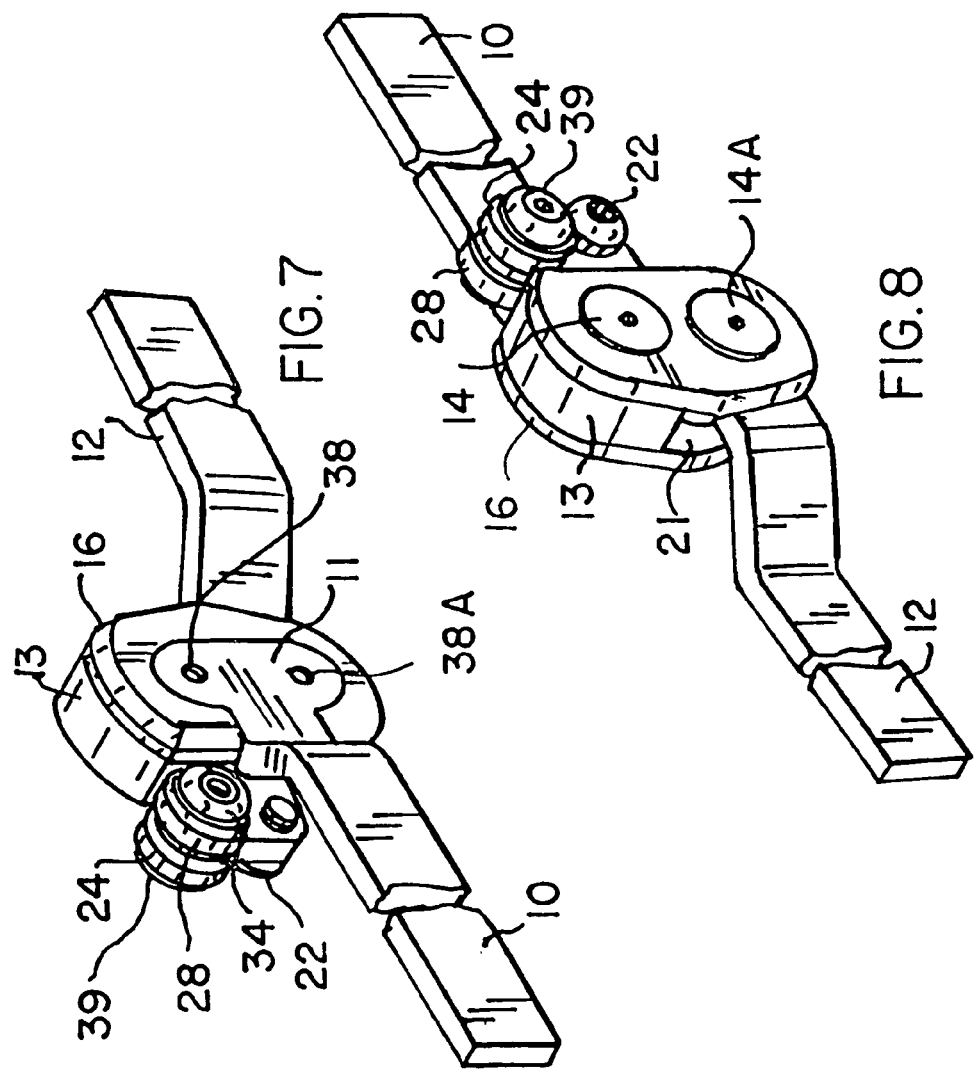

ORTHOTIC HINGE SYSTEM WITH SPRING-BIASED PAWL CONTROL OF RATCHET MEMBER

BACKGROUND OF THE INVENTION

1. Area of the Invention

The present invention relates generally to medical devices and, more particularly, to a hinge system for an orthopedic means for assisting movement of body limbs which are in an infirm or partially infirm state. The invention is of particular utility in infant pediatric and upper extremity applications.

Devices of the type to which the present invention relate are normally referred to as "orthotic". This name is based upon the fact that such devices operate to support or assist injured or infirm body limbs, as opposed to replacing a missing limb. Accordingly, the term orthotic, as used herein, is distinguished from the term prosthesis which generally defines an artificial device to replace a missing body part or limb.

The invention includes a type of orthotic device which operates by a pawl and ratchet, and resilient spring action, to permit a range of certain degrees (steps) of limited rotational movement of infirm limbs relative to each other in a manner intended generally to simulate normal motion of such limbs.

2. Prior Art

This invention is an improvement over that of my U.S. Pat. No. 4,502,472 (1985), and other patents that I hold. Orthotic devices will, typically, include a pair of relatively moveable support members attached respectively to different parts of the body, for example, the upper leg and lower leg; in addition, some form of articulation means providing a resilient, or other controlled or controllable interconnection, between the proximal and distal parts of such a support device, are inherent to an appropriate operation of such devices. For the operation of such devices, it therefore is desirable that any artificial joint means, whether resilient in character or step-advance rotational in character, be sufficiently robust to assist in the effective functioning of the affected limb, while avoiding excesses or insufficiencies of motion which might prove discomforting or injurious, while a certain degree of adjustability, versatility, and the like in the motion of the functioning of such devices, is desirable.

Although the basic function of an orthotic device is to support a limb or limbs, it is desirable to attain a certain limited motion and flexibility in predetermined directions. Thus a goal of orthotic devices is the provision of the fundamental support function while, as an advantageous addition, providing a versatility of motion that will resemble normal body motion. As an addition to enabling adequate support, range of motion, and adjustability to various positions, the orthotic device should be as simple as possible in its arrangement of parts so that ease of manufacture will be attained and the functioning of the device is convenient as possible. The invention also addresses ease of locking and unlocking at given step positions, reverse and forward ratchet locking, unobtrusiveness in appearance of the system, these all being long-felt needs in the art.

SUMMARY OF THE INVENTION

The invention relates to an orthopedic hinge system, comprising an outer and an inner base, each substantially complemental in peripheral dimension to each other, said bases each having a major vertical axis, said inner base having a recess therein, said recess having an axis substantially co-linear with said vertical axes of said bases. Further included is an elongate distal member having a semi-circular pivot end including, upon a portion of said end, ratchet teeth pointing in a counter-clockwise direction, said pivot end rotationally secured to both of said bases; and an elongate proximal member having a transverse end element proportioned for complemental securement within said recess of said inner base, said transverse end element including an axis of rotation co-linear with an axis of rotation of said distal member and defining an axis of rotation of said pivot end of said distal member; a cam lever including a pawl surface having teeth pointing in a clockwise direction and, upon contact with said ratchet teeth of said distal member, complemental therewith, said lever having an axis of rotation co-linear with a second axis within said transverse element of said proximal member, said lever also including a radial projection disposed radially oppositely from said pawl surface.

The system also includes an extension spring having one end secured to said inner base and an opposite end secured to said radial projection of said cam lever, at a distance between ends of said spring causing a bias of said pawl teeth toward engagement with said ratchet teeth and in which counter-clockwise motion of the handle of said cam lever stretches said spring, disengaging said pawl teeth from said ratchet teeth, thus freeing said distal member to rotate relative to said proximal member.

It is the principal object of the invention to provide a hinge means for an orthopedic brace to enable an orthopedic device to accomplish a fundamental support function in pediatric and upper extremity applications while, additionally, providing certain controlled motion in both the extension and flexion directions.

Another object is to provide an orthotic device of the above type having controlled, multi-positional steps rotational motion both reverse and forward ratchet directions.

A further object is to provide a hinge means for an orthotic device having elements which are essentially integral with the normal parts of an orthotic brace and which is easily locked and unlocked.

A still further object of the invention is to provide an orthotic device that is simple and cost-effective to assemble and manufacture.

A further object is to provide an orthotic device that will function unobtrusively and, thereby, afford certain cosmetic advantages to the user.

The above and yet, further objects and advantages of the present invention will become apparent from the hereinafter set forth Detailed Description of the Invention, the Drawings, and Claims appended herewith.

BRIEF DESCRIPTION OF THE DRAWINGS

FIG. 7 is a view, sequential to that of FIG. 6, in which the T-end member has been inserted into the recess of the T-bar securement body shown in FIG. 6.

FIG. 8 is a perspective view in which the system shown in FIG. 7 is rotated 180° about the axis defined by the pivot bushings thereof.

FIG. 11 is a top elevational view of the system shown in FIGS. 8 and 9, along the pivot bushing axis showing the alignment of the rubber "O" Rings to create the unlocking mechanism.

DETAILED DESCRIPTION OF THE INVENTION

Figure 12:
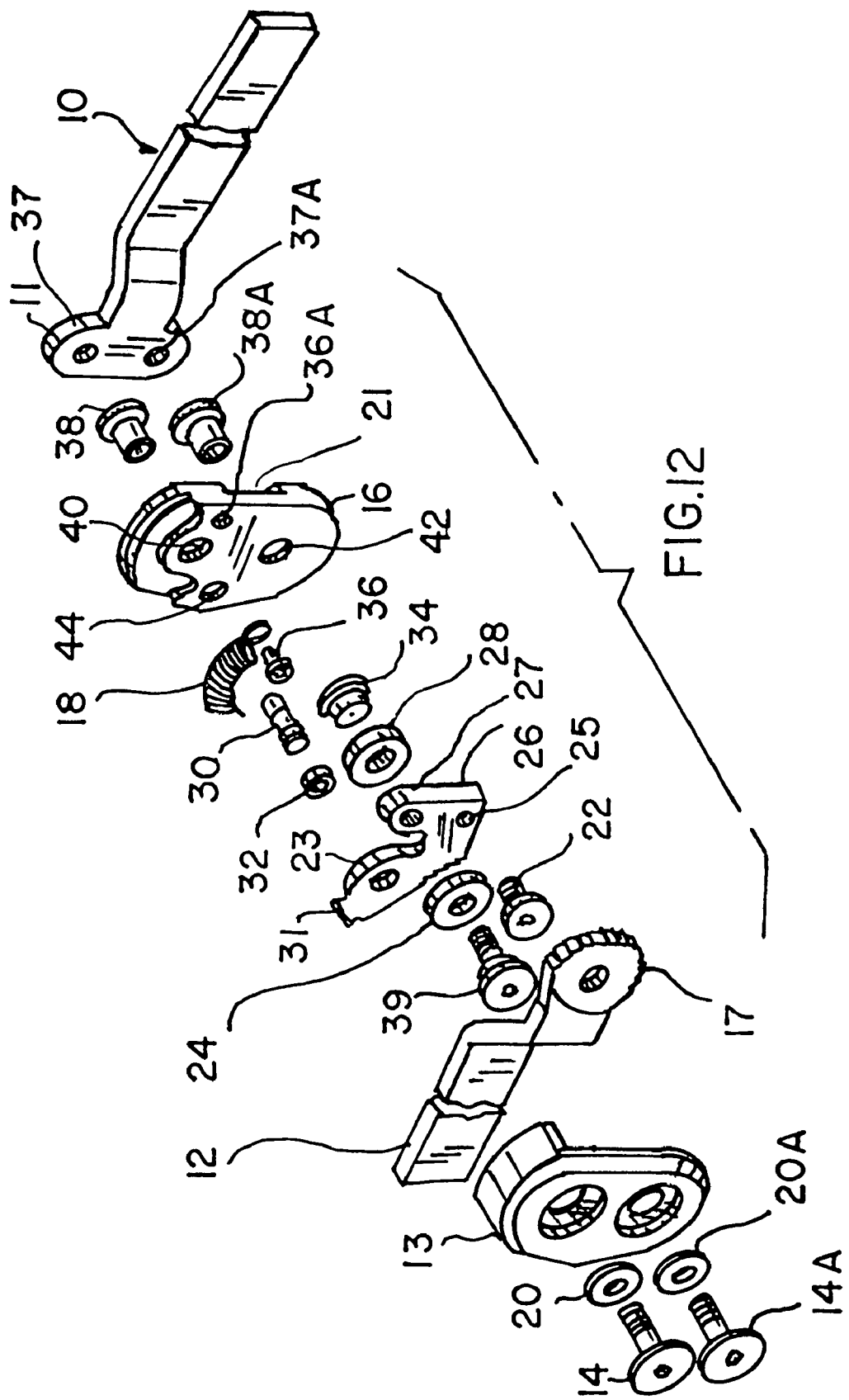
FIG. 12 is an exploded view of the respective components of the inventive system.

With reference to the front breakaway view of FIG. 1 and FIGS. 6 to 10 the inventive orthopedic hinge is shown, and in FIGS. 6-10 with its outer lateral base or main body cover 13. Therein, the principal functional components of the present system may be seen to include a T-bar member (proximal member) 10 which, at an elongate transverse end element or T-end member 11 is press-fittably secured within recess 21 of an inner lateral base or T-end securement body 16. As may be noted in FIGS. 6 and 7, recess 21 within body 16 is complemental to elongate T-end member 11 of elongate T-bar member 10. T-end member 11 is secured to body 16 by upper and lower pivot screws 14 and 14A, through pivot bushings 38 and 38A (see FIGS. 6-8). Thereupon, T-bar member 10 and T-end securement body 16 operate integrally in the hinge system described below. As may be noted (see FIG. 12) pivot bushings 38 and 38A are secured respectively in upper pivot hole 40 and lower pivot hole 42 of T-end securement body 16, thus assuring that elongate proximal member 10 will at all times function rigidly with body 16.

Figure 1:
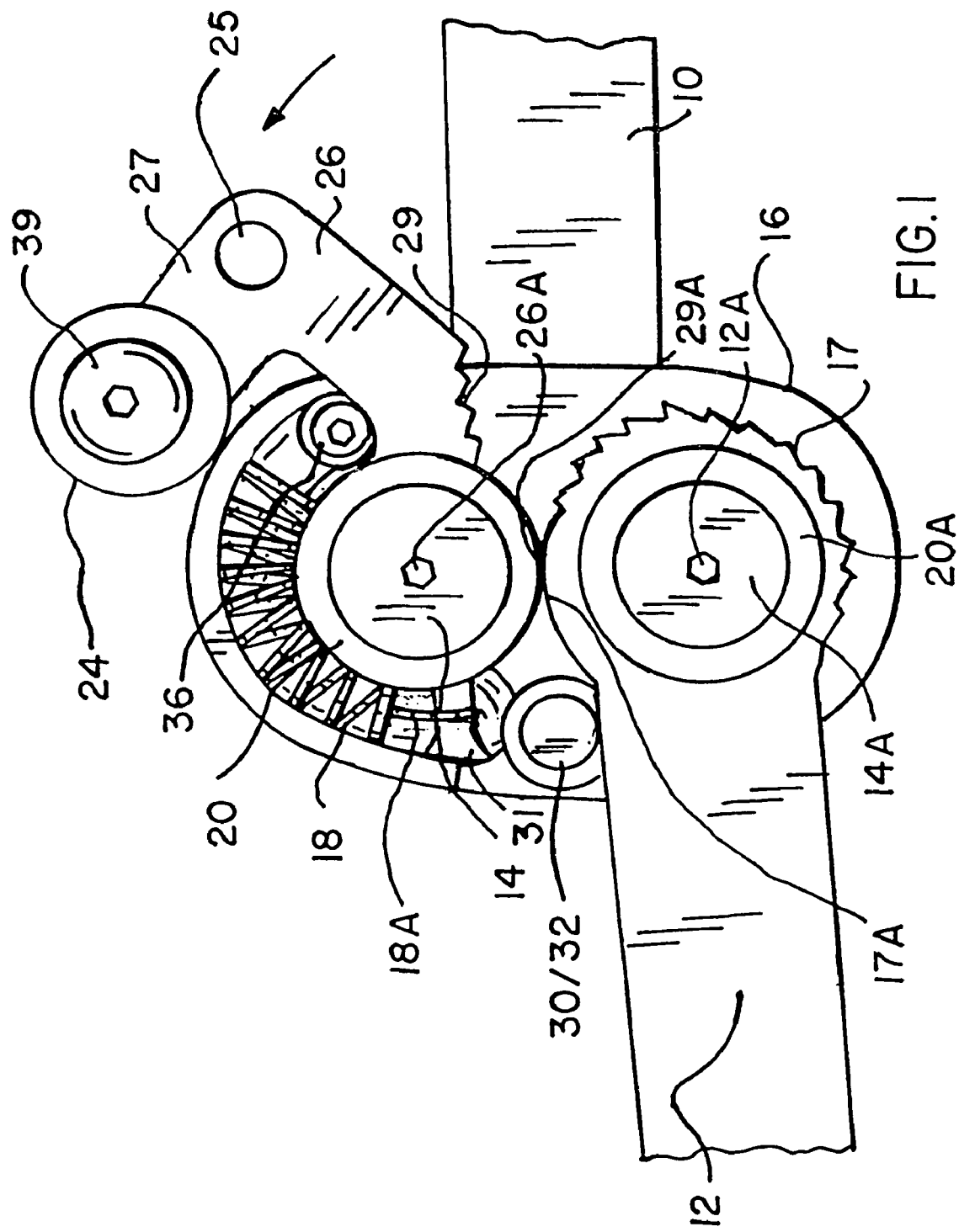
FIG. 1 is a breakaway anterior view of the inventive hinge system showing the spring-biased cam lever thereof and the proximal and distal members in a non-engaged mode and at a 180° angle relative to each other.

Returning to FIG. 1, main body cover or outer lateral base 13 has been removed so that the inner workings of the inventive hinge may be shown. FIG. 1 constitutes a breakaway view of the inventive mechanism taken through main body cover 13. Therein are shown said upper pivot screw 14 and lower pivot screw 14A including pawl washer 20 and ratchet screw washer 20A. With the above understood, FIG. 1 may be seen to further show ratchet (distal) member 12. Integrally included at axis of rotation 12A of distal member 12 is ratchet teeth 17, which, as may be noted in FIG. 1, transcribes approximately 180° of the pivot end of said distal member 12, until the ratchet teeth end at cam surface or non-ratchet surface 17A. As may be further noted, the pivot end of distal member 12 is secured by pivot screw 14A to main body cover 13 of the orthopedic hinge and to above-described T-end securement body 16 (see FIG. 6) of the inventive system.

Rotationally secured to T-bar securement body 16 is a cam lever 26 (see FIGS. 1 to 11) having a pawl surface 29, the cam lever 26 rotationally secured to said T-bar securement body 16 by pivot screw 14. The cam lever 26 is characterized by said pawl surface 29 having pawl teeth pointing in clockwise direction, a cable screw opening 25, a cam handle 27, and washers 24 and 28 which surround a cam lever handle screw 39. 29A is the axis of rotation of the cam lever.

In the view of FIG. 1, pawl surface 29 of cam lever 26 has not engaged ratchet teeth 17 of distal member 12. As such, proximal member 10, which includes its associated elongate T-end member 11, is free to rotate relative to distal member 12, this as may be more fully appreciated with reference to FIGS. 3 and 5A in which the distal member 12 is shown rotated into respective right and acute angles relative to proximal member 10. Accordingly, in the conditions shown in FIGS. 1, 3 and 5A, proximal member 10 and distal member 12 are free to rotate relative to each other since no engagement exists between pawl surface 29 and ratchet teeth 17 of distal member 12.

Figure 2:
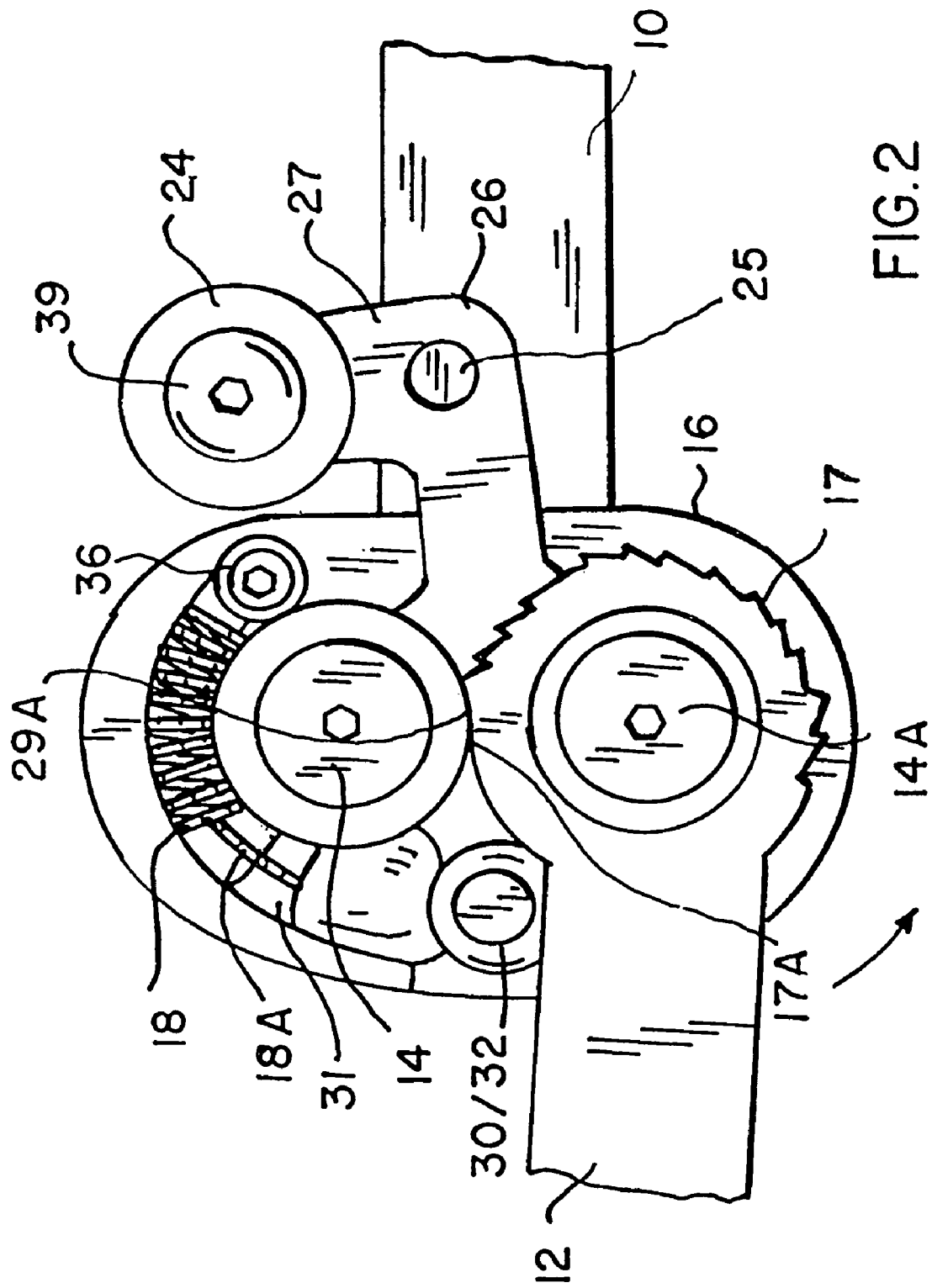
FIG. 2 is a view, similar to that of FIG. 1, however showing the pawl teeth of the cam lever engaged with the ratchet teeth of the distal member.

In FIG. 2, ratchet teeth 17 are shown in abutting relationship with pawl surface 29 of cam lever 26. Therein, it is noted that cam lever 26 includes a radial distal element or radial projection 31 which projects outwardly from the region of left pivot hole 23 of cam lever 26 (see FIGS. 1 and 12). To said radial distal element 31 is attached a first end 18A of an extension spring 18 which, at an opposite end is attached to spring screw 36 that is fastened in opening 36A. The polar curvature of spring 18 is governed by the circumference of the pawl washer 20 which surrounds pivot screw 14. Said screw 14 is then tightened thru pivot hole 40 (see FIGS. 6 and 12) biasing cam lever 26 in a normally closed or engaged position shown in FIGS. 2, 2A, 4 and 5, thereby causing pawl surface 29 of cam lever 26 to complementally engage the teeth of ratchet 17 of distal element 12. When this occurs, the angular position of the distal member 12 relative to the proximal member 10 is fixed. Such fixation may occur at a variety of relative angles as is shown by FIGS. 2, 2A, 4 and 5. Accordingly, by first rotating cam lever 26 upward in the direction of spring 18, it is elongated about the circumference of pawl washer 20. Pawl teeth are then released from the ratchet teeth 17 permitting re-positioning of the angle between the proximal and distal members of the orthopedic hinge. This is shown with reference to FIGS. 1, 5A and 10. Stop pin 30 and its related washer 32 operate, as may be noted with reference to FIGS. 1 to 5A stops with relation to radial distal element 31 of cam lever 26. To re-position distal member 12 relative to the proximal member 10 one must grasp the distal member 12 with one hand, while pressing up the washer 24 (about screw 39) with the thumb while engaging the proximal member 10 with the fingers of the same hand. This motion will result in an extension of the spring 18 about the pawl washer 20 and disengagement of the pawl surface 29 and ratchet teeth 17, as above described, thereby enabling proximal member 10 to rotate freely about said pivot point 12A of the distal member 12 of the orthopedic hinge. It is noted that cam lever 26 rotates about pivot point 26A which is defined by pivot screw 14, and aperture 44 within T-bar securement body 16 at the posterior side of the orthopedic hinge. See FIGS. 1, 3, and 5A. Therein lies one of the many advantages of the instant invention, namely, the pivot bushings 38 and 38A that are recessed within recess 21 of T-bar securement body 16. Thereby all joint pivots, that is, pivot points 12A and 26A of the present invention are incorporated into the T-bar structure of the instant invention. This geometry allows for a compact overall structure of the inventive orthopedic hinge, as shown in FIGS. 7, 8 and 11.

These figures also show other benefits of the invention including the ease of vertical integration of the T-end member 11 into the T-bar securement body 16, the ease of contour of the proximal and distal members 10 and 12 closer to the center plane of the hinge versus those known in the art (see FIG. 11), and particular strength of the orthopedic hinge is achieved by the above-described main body cover 13, T-bar securement body 16, the recessing of pivot screws 14 and 14A within main body cover 13, and the recessing of pivot bushings 38 and 38A (see FIG. 6) within said recess 21 of T-bar securement body 16, while producing the external structure shown in FIGS. 7, 8 and 11. The capability to laterally contour the respective members 10 and 12 is of particular importance with respect to infant, pediatric, and upper extremity adult applications.

It is further noted that the centers of rotation 26A and 12A of pivot screws 14 and 14A respectively define Allen head wrench recesses, thereby providing to the technician or end user, ease of adjustment of the axial rigidity of the proximal and distal members relative to each other as well as the degree of lateral pressure at the radial distal element 31 of the cam lever 26.

Figure 9:
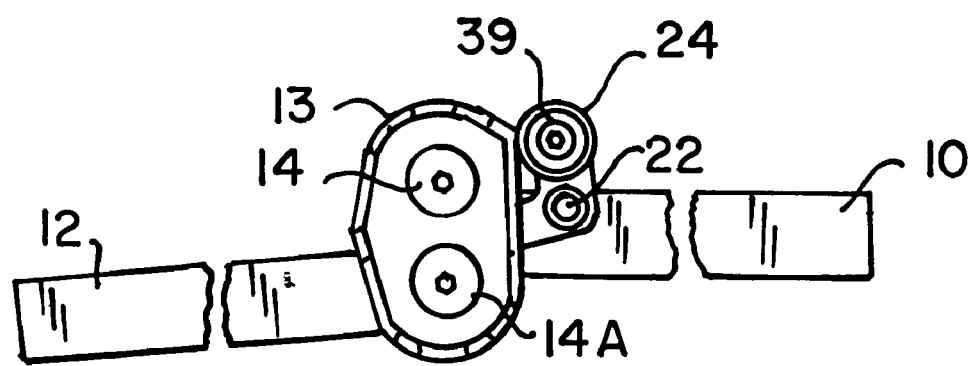
FIG. 9 is a front plan view of the system shown in FIG. 8.
Figure 10:
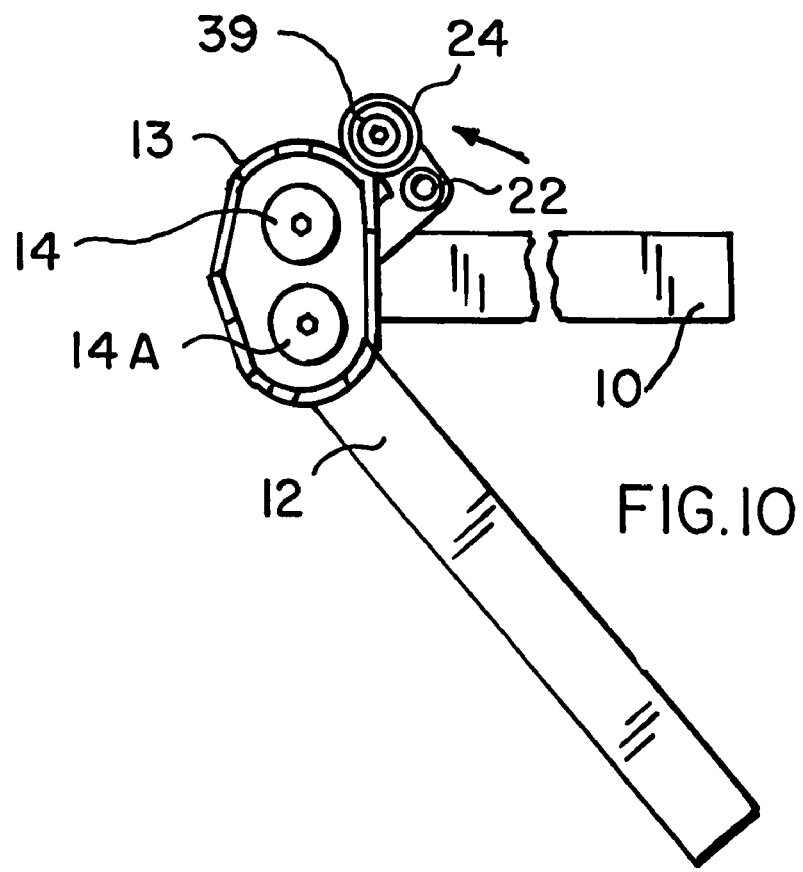
FIG. 10 is a view, sequential to that of FIG. 9, in which the cam lever is rotated upward and counterclockwise thereby releasing the pawl teeth from the ratchet teeth so that the proximal member may be rotated clockwise into a position of approximately 45° relative to the distal member of the system.

External views of the system in respective close and open position from the anterior perspective are shown in FIGS. 9 and 10 respectively.

Figure 2A:
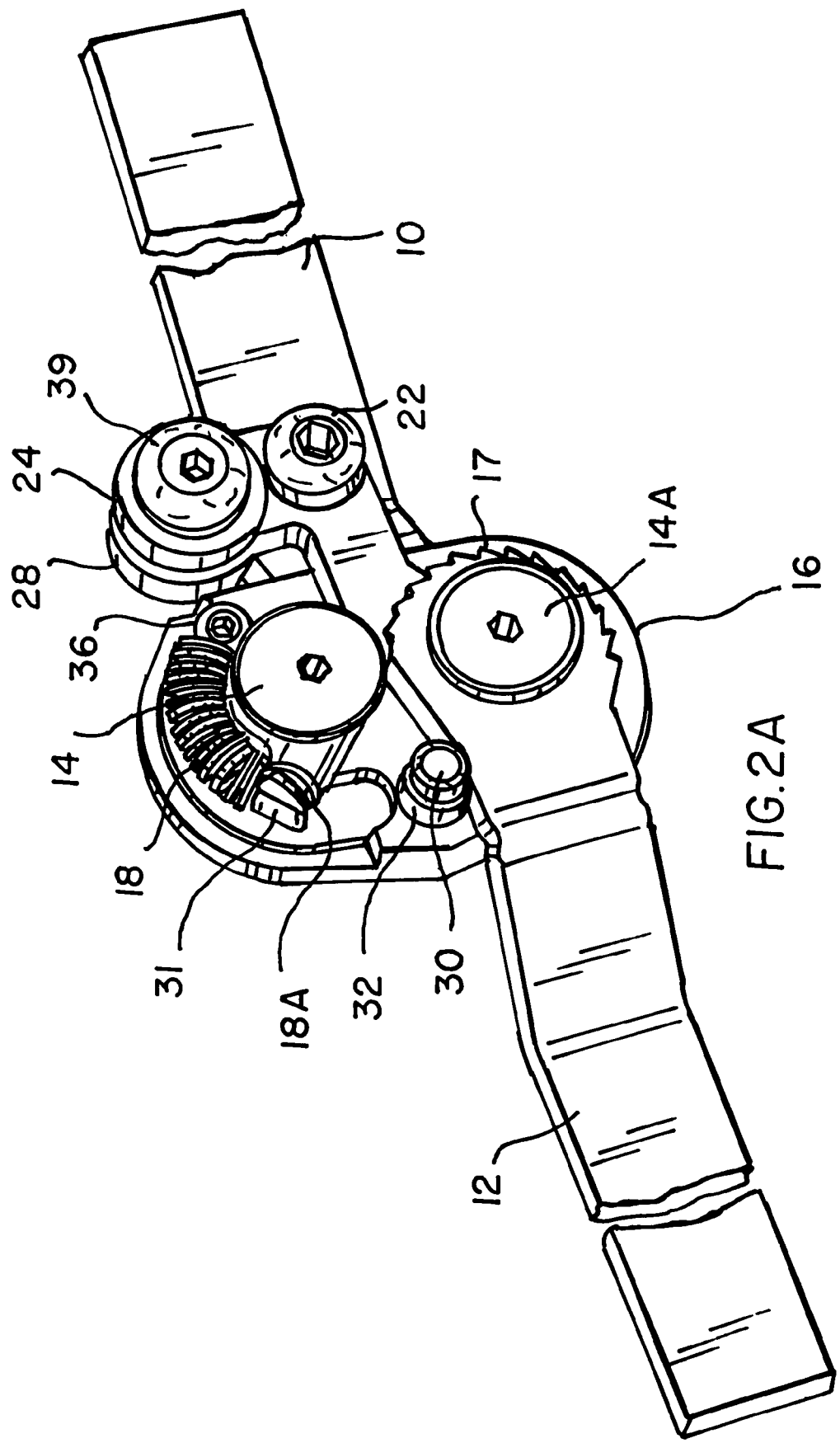
FIG. 2A is a perspective view of the system in the position of FIG. 2.
Figure 3:
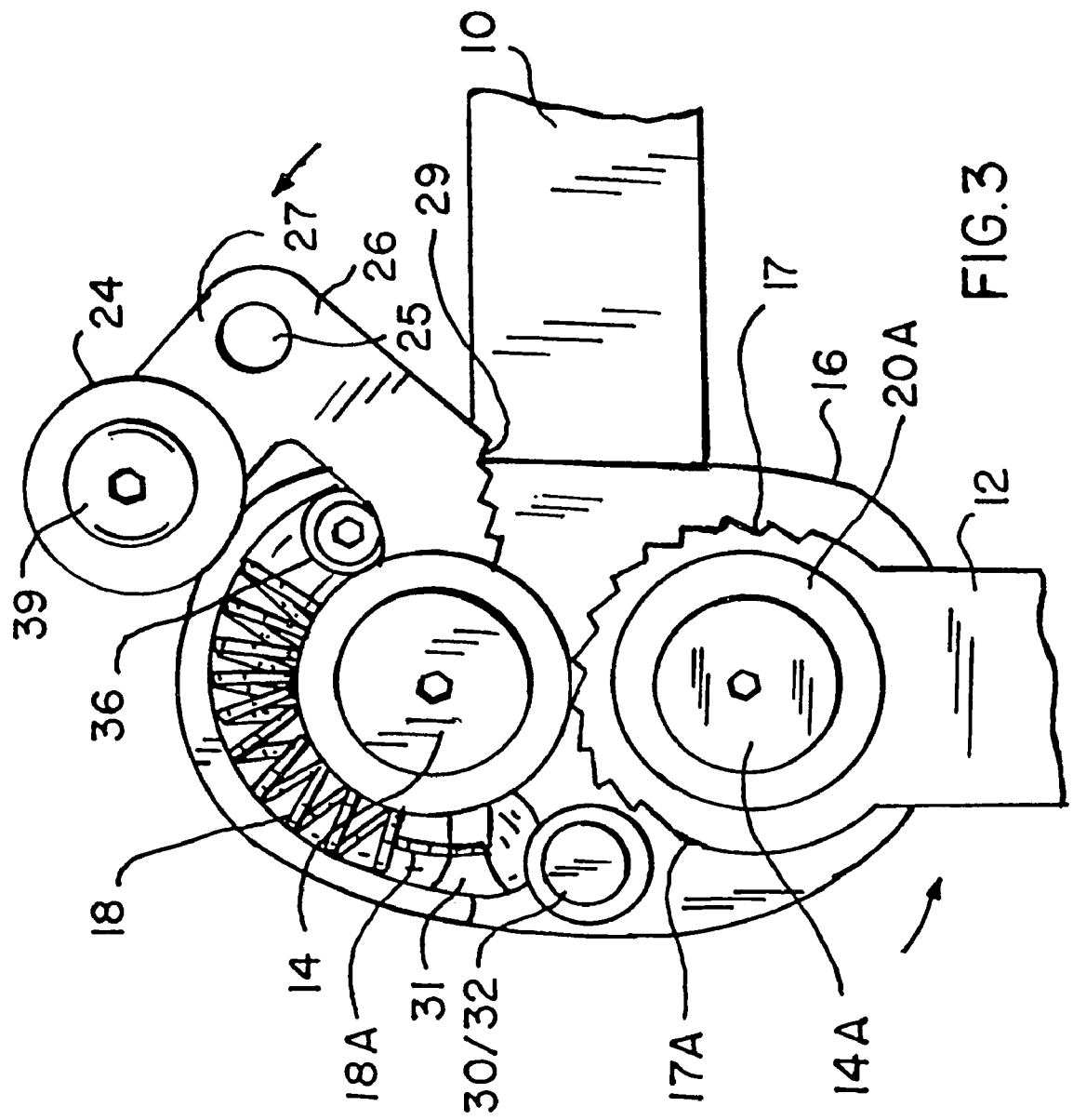
FIG. 3 is a view, similar to that of FIG. 1, however showing rotation of the distal member into a 90° position relative to the proximal or T-end member.
Figure 5:
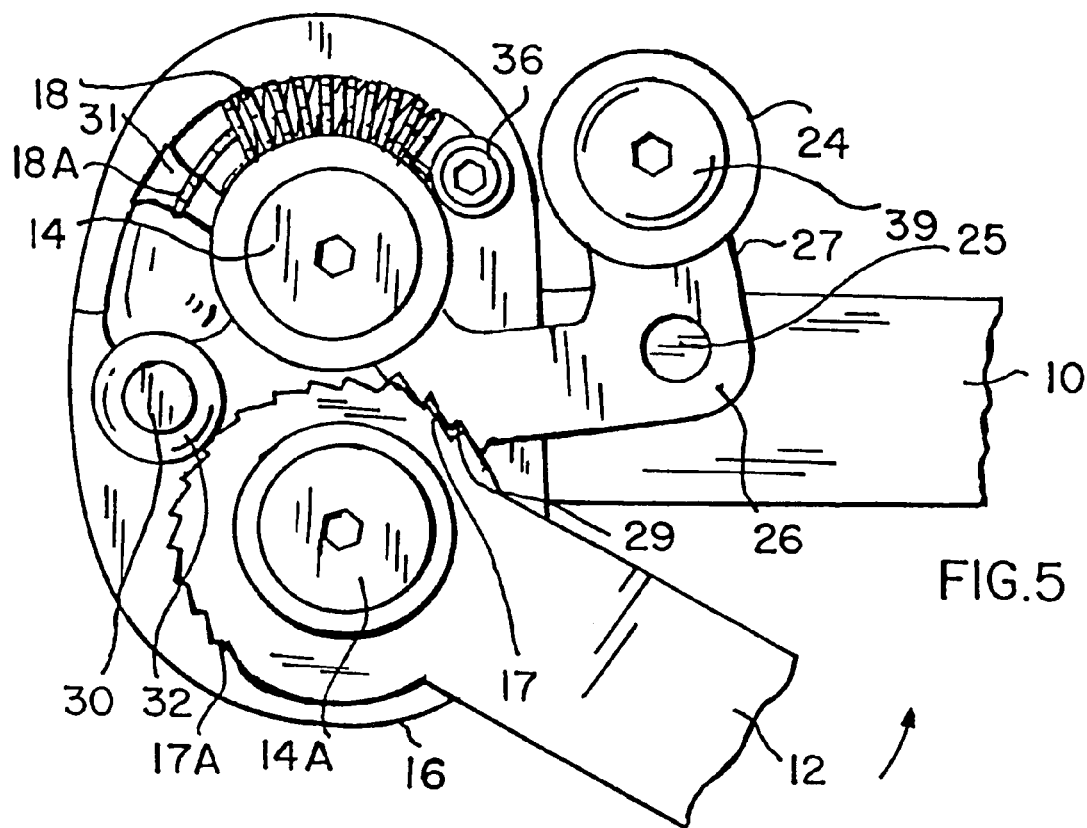
FIG. 5 is a view, similar to that of FIGS. 2 and 4, however showing a counterclockwise, ratchet tooth rotation of the distal member relative to the proximal member of the system.
Figure 4:
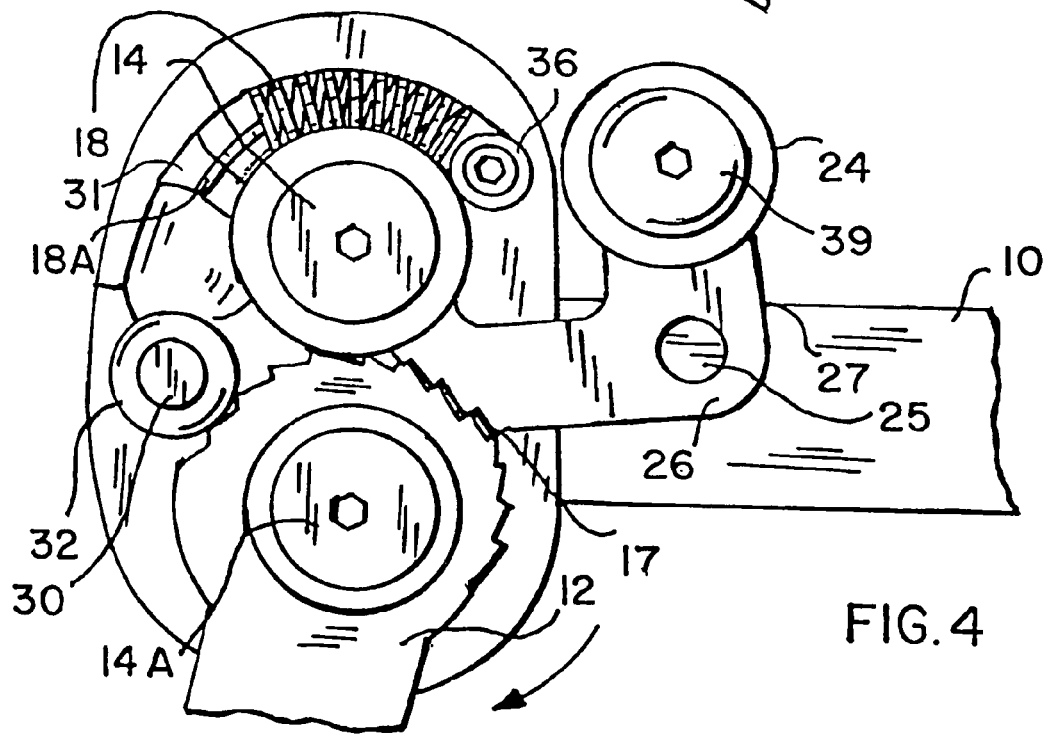
FIG. 4 is a view, similar to that of FIGS. 2 and 2A, however showing a clockwise ratchet rotation of the distal member relative to the proximal member and at a 90° offset therebetween.
Figure 5A:
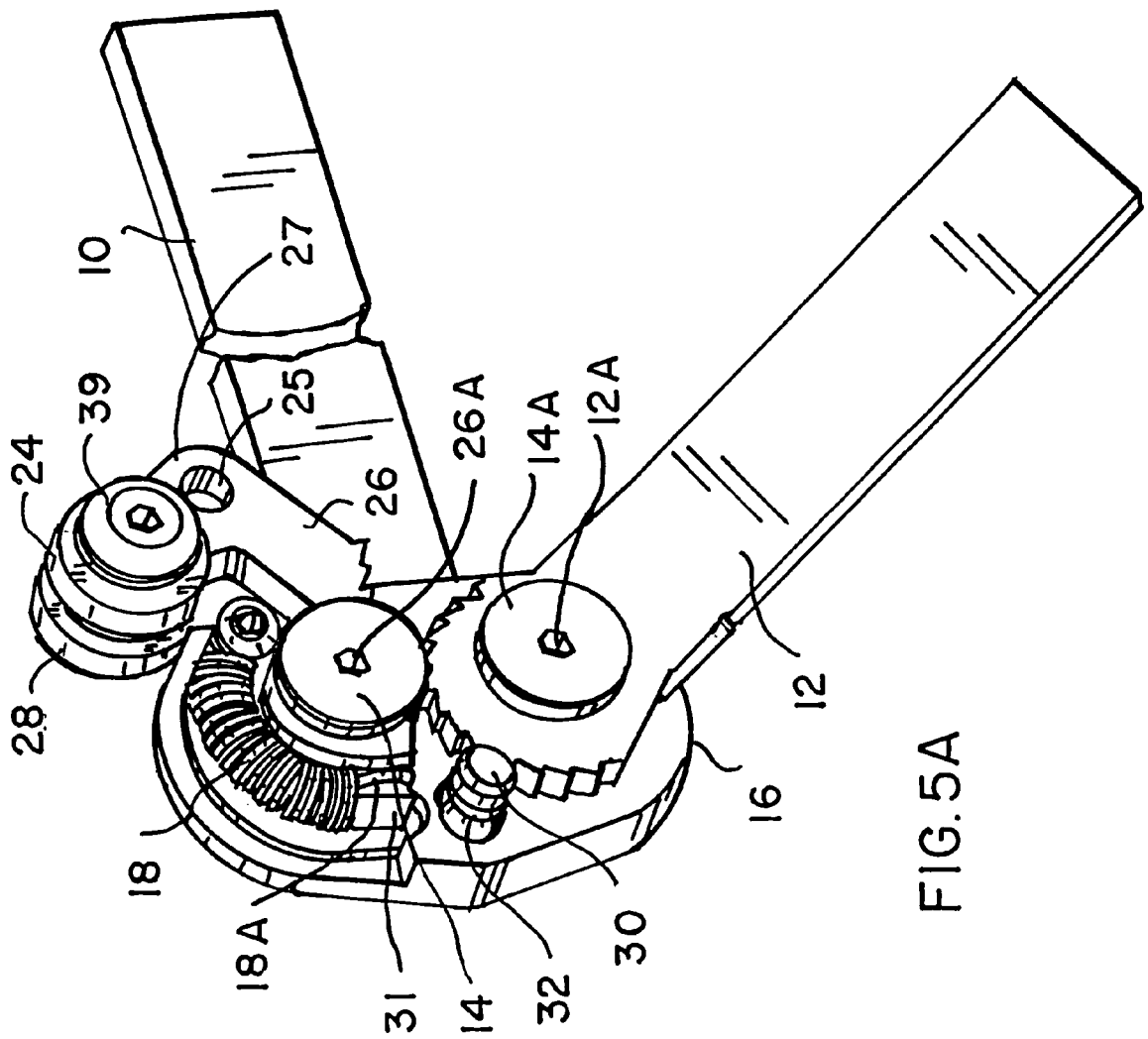
FIG. 5A is a perspective view generally similar to that of FIG. 5, however showing an offset of about 60° between the proximal and distal members of the system, achievable upon release of the pawl teeth from the ratchet teeth when the cam lever is rotated upwardly into the unlocked position. The pawl surface will stay in that position until manually moved to the locked position.
Figure 6:
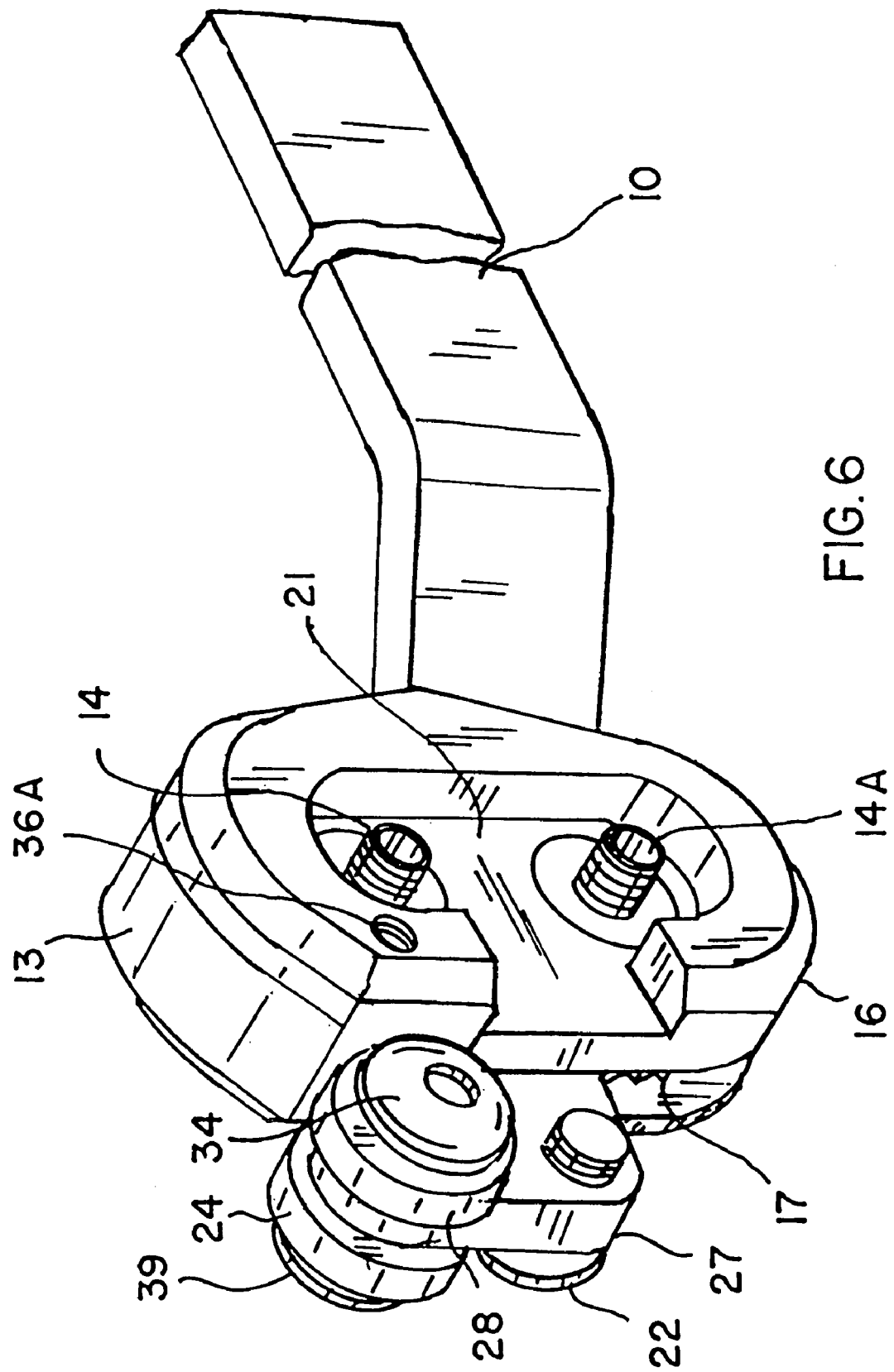
FIG. 6 is an interior view of the inventive hinge system showing the shape of the T-bar securement body and recess therein as proportioned for accommodation of the T-end member. The bushings can be seen to be recessed under the T-end member creating very strong and compact pivot points.

The respective views of potential motion and adjustment of the present system, i.e., FIGS. 1, 2, and 2A showing a 180° relationship between the respective members 10 and 12, FIG. 3 showing a 90° relationship, FIG. 4 showing a 130° degree relationship, FIG. 5 showing a 30° relationship, and FIG. 10 showing a 45° relationship. It is, thereby, to be appreciated that a range of angular adjustment of between 30° and 180° may be achieved through the inventive system.

The versatility of the present system also permits forward ratcheting motion (see FIG. 4) as well as reverse ratcheting motion (see FIGS. 2/2A). Further, spring 18 creates an automatic forward stepping action (see FIG. 4) after re-engagement of the pawl teeth and the ratchet teeth has been established. Further, the system, when the respective members 10 and 12 are in 180° relationship to each other, urges the cam lever 26 into an automatic locking position, as shown in FIGS. 2, 2A, 7, 8, and 9.

The invention also provides a unique unlocking mechanism, effected by the simple application of counterclockwise pressure upon washers 24 and 28 (see FIGS. 3, 5A and 12), creating a detente that will hold the cam lever in an unlocked position until manually released. Cable screw opening 25 provides an additional application of the invention by which a remote cable may be employed to accomplish counterclockwise motion of the cam lever, thereby disengaging the pawl surface of the cam lever from the ratchet teeth of the distal member. When used in a cable mode, cable screw 22 (see FIGS. 6-8 and 12) is employed.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith

Having thus described our invention, what I claim as new, useful and non-obvious is:

1. An orthopedic hinge system, comprising:
   (a) an outer and an inner lateral base, each substantially complemental in peripheral dimension to each other, each of said bases having a major vertical axis, said inner lateral base having a recess therein;
   (b) an elongate distal member having a pivot end including, upon a portion of said pivot end, ratchet teeth pointing in a counter-clockwise direction, said pivot end rotationally secured to both of said outer and inner lateral bases;
   (c) an elongate proximal member having a transverse end element proportioned for complemental securement within said recess of said inner lateral base, said transverse end element including an axis of rotation of said pivot end of said distal member, said axis co-linear with an axis of rotation of said distal member;
   (d) a cam lever including a pawl surface having pawl teeth pointing in a clockwise direction and, upon contact with said ratchet teeth of said distal member, said pawl teeth then complemental therewith, said cam lever having an axis of rotation co-linear with a second axis within said transverse end element of said proximal member, said cam lever also including a radial projection disposed radially oppositely from said pawl surface; and
   (e) an extension spring having one end secured to said inner lateral base and an opposite end, secured to said radial projection of said cam lever, at a distance between ends of said spring causing extension of the spring and a normal bias of said pawl teeth into engagement with said ratchet teeth in which a counterclockwise motion of a handle of said cam lever stretches said spring, disengaging said pawl teeth from said ratchet teeth, and freeing said distal member to rotate relative to said proximal member.

2. The system as recited in claim 1, in which said recess of said inner lateral base exhibits an axis substantially co-linear with a vertical axis of each of said lateral bases.

3. The system as recited in claim 1, in which said pivot end of said distal member includes a non-ratchet surface proportioned for frictional contact with a pawl washer about said axis of rotation of said cam lever.

4. The system as recited in claim 3 comprising a stop pin in counter-clockwise position beyond said radial projection of said cam lever to thereby limit a range of motion of said cam lever and of said non-ratchet surface of said distal member.

5. The system as recited in claim 1, in which said cam lever includes a cable screw opening to which a cable is secured.

* * * * *